United States Patent
Xi et al.

(10) Patent No.: US 11,241,378 B2
(45) Date of Patent: Feb. 8, 2022

(54) PHARMACEUTICAL JAK KINASE INHIBITOR AND DIETHYLENE GLYCOL COMPOSITION FOR TOPICAL ADMINISTRATION AND PREPARATION METHOD THEREFOR

(71) Applicant: JIANGSU HENGRUI MEDICINE CO., LTD., Jiangsu (CN)

(72) Inventors: Honglei Xi, Jiangsu (CN); Qiudong Jiang, Jiangsu (CN)

(73) Assignee: Jiangsu Hengrui Medicine Co., Ltd., Jiangsu (CN)

( * ) Notice: Subject to any disclaimer, the term of this patent is extended or adjusted under 35 U.S.C. 154(b) by 50 days.

(21) Appl. No.: 16/765,227

(22) PCT Filed: Nov. 19, 2018

(86) PCT No.: PCT/CN2018/116197
§ 371 (c)(1),
(2) Date: May 19, 2020

(87) PCT Pub. No.: WO2019/096303
PCT Pub. Date: May 23, 2019

(65) Prior Publication Data
US 2020/0276109 A1   Sep. 3, 2020

(30) Foreign Application Priority Data
Nov. 20, 2017   (CN) .......................... 201711160777.4

(51) Int. Cl.
*A61K 9/00* (2006.01)
*A61K 9/16* (2006.01)
*A61K 31/519* (2006.01)

(52) U.S. Cl.
CPC .......... *A61K 9/0014* (2013.01); *A61K 9/1617* (2013.01); *A61K 9/1623* (2013.01); *A61K 9/1641* (2013.01); *A61K 9/1652* (2013.01); *A61K 31/519* (2013.01)

(58) Field of Classification Search
CPC .. A61K 9/0014; A61K 9/1623; A61K 9/1641; A61K 9/1652; A61K 9/06; A61K 31/519; A61P 17/06
See application file for complete search history.

(56) References Cited

FOREIGN PATENT DOCUMENTS

| EP | 3006445 A1 | 4/2016 |
|---|---|---|
| WO | 2014194741 A1 | 12/2013 |
| WO | 2014194741 A1 * | 12/2014 |

OTHER PUBLICATIONS

Ying et al, Mechanism of Trancutal as Enhancer for Percutaneous Absorption, The Chinese Journal of Modern Applied Pharmacy, No. 1, pp. 23-25' (Year: 2004).*
Javadzadeh, Y, et al, "Enhancing percutaneous delivery of methotrexate using different types of surfactants," Colloids and Surfaces B: Biointerfaces, Elsevier, Amsterdam, NL vol. 82, No. 2, Feb. 1, 2011.
Yu, Zhong et al., "Clinical Research Progress of JAK Inhibitor", (Strait Pharmaceutical Journal, vol. 24, No. (1), Dec. 31, 2012 pp. 19-20, sections 2.1-2.3.
Wu, Ying et al., "Application and Mechanism of Transcutol as Enhancer for Percutaneous Absorption" (Chinese Journal of Modern Applied Pharmacy), vol. 21, No. (1), Feb. 29, 2004.
International Search Report dated Feb. 15, 2019 for PCT/CN2018/116197.

* cited by examiner

*Primary Examiner* — Carlos A Azpuru
(74) *Attorney, Agent, or Firm* — Ice Miller LLP

(57) ABSTRACT

A pharmaceutical composition for topical administration and a preparation method therefor are described. In particular, a pharmaceutical composition comprising (3aR,5s,6aS)-N-(3-methoxy-1,2,4-thiadiazol-5-yl)-5-(methyl(7H-pyrrolo[2,3-d]pyrimidin-4-yl)amino)hexahydrocyclopenta[c]pyrrole-2(1H)-carboxamide, or a pharmaceutically acceptable salt thereof, and diethylene glycol monoethyl ether is described.

21 Claims, No Drawings

PHARMACEUTICAL JAK KINASE INHIBITOR AND DIETHYLENE GLYCOL COMPOSITION FOR TOPICAL ADMINISTRATION AND PREPARATION METHOD THEREFOR

CROSS-REFERENCE TO RELATED APPLICATIONS

This application is a Section 371 of International Patent Application No. PCT/CN2018/116197, filed Nov. 19, 2018, which was published in the Chinese language on May 23, 2019, under International Publication No. WO 2019/096303 A1, which claims priority under 35 U.S.C. § 119(b) to Chinese Patent Application No. 201711160777.4, filed Nov. 20, 2017, the disclosure of all of which are incorporated herein by reference in their entireties.

FIELD OF THE INVENTION

The present disclosure belongs to the pharmaceutical preparation field, and particularly relates to a pharmaceutical composition of (3aR,5s,6aS)-N-(3-methoxy-1,2,4-thiadiazol-5-yl)-5-(methyl(7H-pyrrolo[2,3-d]pyrimidin-4-yl)amino)hexahydrocyclopenta[c]pyrrole- 2(1H)-carboxamide or a pharmaceutically acceptable salt thereof, and diethylene glycol monoethyl ether.

BACKGROUND OF THE INVENTION

Psoriasis is a common stubborn and recurrent chronic non-infectious inflammatory skin disease characterized by excessive epidermal hyperplasia. The total prevalence in China is about 0.4%, and the prevalence in Europe and the United States reaches 2% to 3%. The disease has no gender difference, and about ⅓ of the patients have a family genetic history. Among them, the incidence of psoriasis vulgaris accounts for more than 95% of psoriasis. Since the early clinical manifestation of psoriasis is mainly epidermal hyperplasia, the main purpose of traditional therapeutic medicaments including methotrexate and hydroxyurea is to inhibit epidermal hyperplasia and anti-inflammation. With the deepening of the research on the molecular mechanism of psoriasis, the targets for the development and research of new medicaments for psoriasis are diversified, including tumor necrosis factor α (TNF-α), phosphodiesterase 4 (PDE4), Janus kinase JAK, and interleukin and its receptor (IL&ILR) etc.

Janus kinase JAK is a non-receptor tyrosine kinase which participates in the signal transduction of various cytokines and is the key to the JAK-signal transduction and transcription activator (JAK/ATART) pathway of cytokine-induced biological effects, and it plays a key role in various cytokine-induced biological processes including hematopoiesis and inflammatory response. Therefore, inhibition of JAK may have a therapeutic effect on psoriasis. External JAK inhibitors currently under development at home and abroad include Ruxolitinib phosphate cream, and Tofacitinib ointment.

CN104470927B discloses a JAK inhibitor compound (3aR,5s,6aS)-N-(3-methoxy-1,2,4-thiadiazol-5-yl)-5-(methyl(7H-pyrrolo[2,3-d]pyrimidin-4-yl)amino)hexahydrocyclopenta[c]pyrrole- 2(1H)-carboxamide or a pharmaceutically acceptable salt thereof, which has a good activity and has the following formula:

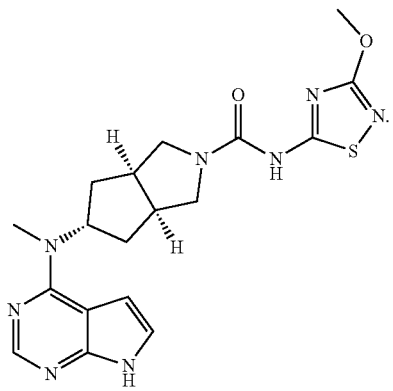 [SMILES: COc1nsc(NC(=O)N2C[C@H]3C[C@H](N(C)c4ncnc5[nH]ccc45)C[C@H]3C2)n1]

The key to the success of treating skin diseases by topical administration lies in that not only can the medicament penetrate the stratum corneum to reach the diseased region, but also the medicament can maintain the therapeutic effect for a period of time. However, (3aR,5s,6aS)-N-(3-methoxy-1,2,4-thiadiazol-5-yl)-5-(methyl(7H-pyrrolo[2,3-d]pyrimidin-4-yl)amino)hexahydrocyclopenta[c]pyrrole- 2(1H)-carboxamide or a pharmaceutically acceptable salt thereof has a poor ability to penetrate the skin barrier and stay in the skin, and the pharmaceutical composition thereof has a risk of uneven content. The present disclosure provides a pharmaceutical composition comprising a JAK inhibitor and a preparation method thereof to solve the above problems.

SUMMARY OF THE INVENTION

The present disclosure provides a pharmaceutical composition comprising an active ingredient (3aR,5s,6aS)-N-(3-methoxy-1,2,4-thiadiazol-5-yl)-5-(methyl(7H-pyrrolo[2,3-d]pyrimidin-4-yl)amino)hexahydrocyclopenta[c]pyrrole- 2(1H)-carboxamide or a pharmaceutically acceptable salt thereof, and diethylene glycol monoethyl ether.

In optional embodiments, the content of diethylene glycol ethyl ether is 0.5% to 20%, and can be 0.5%, 0.6%, 0.7%, 0.8%, 0.9%, 1.0%, 1.5%, 2.0%, 2.5%, 3.0%, 3.5%, 4.0%, 4.5%, 5.0%, 5.5%, 6.0%, 6.5%, 7.0%, 7.5%, 8.0%, 8.5%, 9.0%, 9.5%, 10.0%, 10.5%, 11.0%, 11.5%, 12.0%, 12.5%, 13.0%, 13.5%, 14.0%, 14.5%, 15.0%, 15.5%, 16.0%, 16.5%, 17.0%, 17.5%, 18.0%, 18.5%, 19.0%, 19.5% or 20.0%, preferably 1% to 10%, based on the total weight of the pharmaceutical composition.

The pharmaceutical composition of the present disclosure can further comprise a matrix, the matrix can be a water-soluble matrix, preferably contains a polyethylene glycols macromolecular compound, and the average molecular weight of the polyethylene glycols macromolecular compound can be 100 to 6000. In optional embodiments, the average molecular weight can be 100, 200, 300, 400, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 5100, 5200, 5300, 5400, 5500, 5600, 5700, 5800, 5900 or 6000.

In preferred embodiments, the matrix can contain polyethylene glycol 400 and polyethylene glycol 4000, and the weight ratio of polyethylene glycol 400 to polyethylene glycol 4000 is 1:10 to 10:1, preferably 1:5 to 5:1, to adjust the ointment to achieve a suitable viscosity and spreadability, and to ensure the content uniformity of the active ingredient.

Further, in optional embodiments, the content of the matrix is 40% to 90%, and can be 40.0%, 40.5%, 41.0%, 41.5%, 42.0%, 42.5%, 43.0%, 43.5%, 44.0%, 44.5%, 45.0%, 45.5%, 46.0%, 46.5%, 47.0%, 47.5%, 48.0%, 48.5%, 49.0%, 49.5%, 50.0%, 50.5%, 51.0%, 51.5%, 52.0%, 52.5%, 53.0%, 53.5%, 54.0%, 54.5%, 55.0%, 55.5%, 56.0%, 56.5%, 57.0%, 57.5%, 58.0%, 58.5%, 59.0%, 59.5%, 60.0%, 60.5%, 61.0%, 61.5%, 62.0%, 62.5%, 63.0%, 63.5%, 64.0%, 64.5%, 65.0%, 65.5%, 66.0%, 66.5%, 67.0%, 67.5%, 68.0%, 68.5%, 69.0%, 69.5%, 70.0%, 70.5%, 71.0%, 71.5%, 72.0%, 72.5%, 73.0%, 73.5%, 74.0%, 74.5%, 75.0%, 75.5%, 76.0%, 76.5%, 77.0%, 77.5%, 78.0%, 78.5%, 79.0%, 79.5%, 80.0%, 80.5%, 81.0%, 81.5%, 82.0%, 82.5%, 83.0%, 83.5%, 84.0%, 84.5%, 85.0%, 85.5%, 86.0%, 86.5%, 87.0%, 87.5%, 88.0%, 88.5%, 89.0%, 89.5% or 90.0%, preferably 50% to 80%, based on the total weight of the pharmaceutical composition.

In optional embodiments, the content of the active ingredient is about 0.1% to 20%, and can be 0.10%, 0.16%, 0.21%, 0.26%, 0.31%, 0.36%, 0.41%, 0.46%, 0.51%, 0.56%, 0.61%, 0.66%, 0.71%, 0.76%, 0.81%, 0.86%, 0.91%, 0.96%, 0.41%, 0.43%, 0.45%, 0.47%, 0.49%, 0.51%, 0.53%, 0.55%, 0.57%, 0.59%, 0.61%, 0.63%, 0.65%, 0.67%, 0.69%, 0.71%, 0.73%, 0.75%, 0.77%, 0.79%, 0.81%, 0.83%, 0.85%, 0.87%, 0.89%, 0.91%, 0.93%, 0.95%, 0.97%, 0.99%, 1.0%, 1.5%, 2.0%, 2.5%, 3.0%, 3.5%, 4.0%, 4.5%, 5.0%, 5.5%, 6.0%, 6.5%, 7.0%, 7.5%, 8.0%, 8.5%, 9.0%, 9.5%, 10.0%, 10.5%, 11.0%, 11.5%, 12.0%, 12.5%, 13.0%, 13.5%, 14.0%, 14.5%, 15.0%, 15.5%, 16.0%, 16.5%, 17.0%, 17.5%, 18.0%, 18.5%, 19.0%, 19.5% or 20.0%, preferably about 0.1% to 10%, based on the total weight of the pharmaceutical composition.

Further, the pharmaceutical composition of the present disclosure further comprises an additive. The additive is well known to those skilled in the art, and is at least one selected from, but not limited to, the group consisting of preservatives, humectants and antioxidants.

The preservative of the present disclosure is known or identifiable to those skilled in the art, and is at least one selected from, but not limited to, the group consisting of methylparaben, ethylparaben, benzoic acid, sorbic acid, phenoxyethanol, trichloro-tert-butylalcohol, phenylmercuric acetate, phenol, cresol, and benzalkonium chloride, and the content of the preservative is preferably 0.05% to 0.5%, and can be 0.05%, 0.06%, 0.07%, 0.08%, 0.09%, 0.10%, 0.11%, 0.12%, 0.13%, 0.14%, 0.15%, 0.16%, 0.17%, 0.18%, 0.19%, 0.20%, 0.21%, 0.22%, 0.23%, 0.24%, 0.25%, 0.26%, 0.27%, 0.28%, 0.29%, 0.30%, 0.31%, 0.32%, 0.33%, 0.34%, 0.35%, 0.36%, 0.37%, 0.38%, 0.39%, 0.40%, 0.41%, 0.42%, 0.43%, 0.44%, 0.45%, 0.46%, 0.47%, 0.48%, 0.49% or 0.50%, based on the total weight of the pharmaceutical composition.

The humectant of the present disclosure is known or identifiable to those skilled in the art, and is at least one selected from, but not limited to, the group consisting of glycerol, propylene glycol, 1,3-butanediol, sorbitol, xylitol, hyaluronic acid and trehalose, and the content of the humectant is preferably 20% to 60%, and can be 20.0%, 20.5%, 21.0%, 21.5%, 22.0%, 22.5%, 23.0%, 23.5%, 24.0%, 24.5%, 25.0%, 25.5%, 26.0%, 26.5%, 27.0%, 27.5%, 28.0%, 28.5%, 29.0%, 29.5%, 30.0%, 30.5%, 31.0%, 31.5%, 32.0%, 32.5%, 33.0%, 33.5%, 34.0%, 34.5%, 35.0%, 35.5%, 36.0%, 36.5%, 37.0%, 37.5%, 38.0%, 38.5%, 39.0%, 39.5%, 40.0%, 40.5%, 41.0%, 41.5%, 42.0%, 42.5%, 43.0%, 43.5%, 44.0%, 44.5%, 45.0%, 45.5%, 46.0%, 46.5%, 47.0%, 47.5%, 48.0%, 48.5%, 49.0%, 49.5%, 50.0%, 50.5%, 51.0%, 51.5%, 52.0%, 52.5%, 53.0%, 53.5%, 54.0%, 54.5%, 55.0%, 55.5%, 56.0%, 56.5%, 57.0%, 57.5%, 58.0%, 58.5%, 59.0%, 59.5% or 60.0%, based on the total weight of the pharmaceutical composition.

The antioxidant of the present disclosure is known or identifiable to those skilled in the art, and is at least one selected from, but not limited to, the group consisting of butylated hydroxyanisole, butylated hydroxytoluene, propyl gallate and tocopherol, and the content of the antioxidant is preferably 0.05% to 0.5%, and can be 0.05%, 0.06%, 0.07%, 0.08%, 0.09%, 0.10%, 0.11%, 0.12%, 0.13%, 0.14%, 0.15%, 0.16%, 0.17%, 0.18%, 0.19%, 0.20%, 0.21%, 0.22%, 0.23%, 0.24%, 0.25%, 0.26%, 0.27%, 0.28%, 0.29%, 0.30%, 0.31%, 0.32%, 0.33%, 0.34%, 0.35%, 0.36%, 0.37%, 0.38%, 0.39%, 0.40%, 0.41%, 0.42%, 0.43%, 0.44%, 0.45%, 0.46%, 0.47%, 0.48%, 0.49% or 0.50%, based on the total weight of the pharmaceutical composition.

In optional embodiments, the pharmaceutical composition comprises:

i) 0.1% w/w to 20% w/w % w/w of the active ingredient (3aR,5s,6aS)-N-(3-methoxy-1,2,4-thiadiazol-5-yl)-5-(methyl(7H-pyrrolo[2,3-d]pyrimidin-4-yl)amino)hexahydrocyclopenta[c]pyrrole- 2(1H)-carboxamide or a pharmaceutically acceptable salt thereof, and ii) 0.5% w/w to 20% w/w of diethylene glycol monoethyl ether.

In optional embodiments, the pharmaceutical composition comprises:

i) 0.1% w/w to 20% w/w of the active ingredient (3aR, 5s,6aS)-N-(3-methoxy-1,2,4-thiadiazol-5-yl)-5-(methyl (7H-pyrrolo[2,3-d]pyrimidin-4-yl)amino)hexahydrocyclopenta[c]pyrrole- 2(1H)-carboxamide or a pharmaceutically acceptable salt thereof, ii) 0.5% w/w to 20% w/w of diethylene glycol monoethyl ether, and iii) 40% w/w to 90% w/w of a water-soluble matrix, the water-soluble matrix preferably contains polyethylene glycol 400 and polyethylene glycol 4000.

In optional embodiments, the pharmaceutical composition comprises:

i) 0.1% w/w to 20% w/w of the active ingredient (3aR, 5s,6aS)-N-(3-methoxy-1,2,4-thiadiazol-5-yl)-5-(methyl (7H-pyrrolo[2,3-d]pyrimidin-4-yl)amino)hexahydrocyclopenta[c]pyrrole- 2(1H)-carboxamide or a pharmaceutically acceptable salt thereof, ii) 0.5% w/w to 20% w/w of diethylene glycol monoethyl ether, iii) 40% w/w to 90% w/w of a water-soluble matrix, the water-soluble matrix preferably contains polyethylene glycol 400 and polyethylene glycol 4000, and iv) 20% w/w to 60% w/w of a humectant, the humectant is preferably at least one selected from the group consisting of methylparaben, ethylparaben, benzoic acid, sorbic acid, phenoxyethanol, trichloro-tert-butylalcohol, phenylmercuric acetate, phenol, cresol and benzalkonium chloride.

Further, the particle size of the active ingredient in the pharmaceutical composition of the present disclosure is not greater than 50 μm, and can be 50, 48, 46, 44, 42, 40, 38, 36, 34, 32, 30, 28, 26, 24, 22, 20, 18, 16, 14, 12, 10, 8, 6, 4 or 2 μm, preferably not greater than 30 μm, more preferably not greater than 20 μm.

The present disclosure also provides a method for preparing the pharmaceutical composition comprising:
i) mixing the active ingredient (3aR,5s,6aS)-N-(3-methoxy-1,2,4-thiadiazol-5-yl)-5-(methyl(7H-pyrrolo[2,3-d]pyrimidin-4-yl)amino)hexahydrocyclopenta[c]pyrrole-2(1H)-carboxamide or a pharmaceutically acceptable salt thereof, diethylene glycol monoethyl ether and at least one pharmaceutical excipient optionally selected from the group consisting of matrices, antioxidants and preservatives, and
ii) filling the mixture obtained in step i).

The present disclosure also provides a use of the pharmaceutical composition in the manufacture of a medicament for treating or preventing an immune system disorder or disease.

The immune system disorder or disease can be selected from immune system diseases including, for example, organ transplant rejection (e.g., allogeneic inhibition rejection and graft-versus-host disease); autoimmune disorders including, for example, lupus, multiple sclerosis, rheumatoid arthritis, juvenile arthritis, psoriasis, ulcerative colitis, Crohn's disease, autoimmune thyroid disease, etc.; skin diseases including, for example, psoriasis, rash, atopic dermatitis, etc.; allergic conditions including, for example, asthma, rhinitis, etc.; viral diseases including, for example, hepatitis B, hepatitis C, varicella-zoster virus, etc.; type I diabetes and diabetic complications; Alzheimer's disease, xerophthalmia, myelofibrosis, thrombocytosis, erythrocytosis or leukemia; cancers including, for example, solid tumors (e.g., prostate cancer, kidney cancer, liver cancer, pancreatic cancer, gastric cancer, breast cancer, lung cancer, head and neck cancer, thyroid cancer, glioblastoma, melanoma, etc.), blood cancer (e.g., lymphoma, leukemia, etc.), skin cancer (e.g., cutaneous T-cell lymphoma, cutaneous B-cell lymphoma, etc.

In some embodiments, provided herein is a use of the pharmaceutical composition in the manufacture of a medicament for treating a skin disease.

In the present disclosure, the pharmaceutically acceptable salt of (3aR,5s,6aS)-N-(3-methoxy-1,2,4-thiadiazol-5-yl)-5-(methyl(7H-pyrrolo[2,3-d]pyrimidin-4-yl)amino)hexahydrocyclopenta[c]pyrrole- 2(1H)-carboxamide can be selected from, but not limited to, hydrochloride, maleate, hydrobromide, p-toluenesulfonate, mesylate, sulfate or ethanesulfonate.

In the present disclosure, the "average molecular weight" adopts the weight-average molecular weight of the polymer, which is a statistical average value based on the mass fraction of components of each grade in the polymer. It can be calculated by the following formula:

$$Mw = \sum W_i M_i = \frac{\Sigma N_i W_i^2}{\Sigma N_i W_i},$$

wherein $W_i$ is the mass fraction of the components with a molar mass of $M_i$ grade, and $N_i$ is the molar fraction of the components with a molar mass of $M_i$ grade.

The pharmaceutical excipients or reagents of the present disclosure can be obtained from commercial sources, such as diethylene glycol monoethyl ether; the compound (3aR,5s,6aS)-N-(3-methoxy-1,2,4-thiadiazol-5-yl)-5-(methyl(7H-pyrrolo[2,3-d]pyrimidin-4-yl)amino)hexahydrocyclopenta[c]pyrrole- 2(1H)-carboxamide can be prepared by reference to the method described in CN103415520B.

DETAILED DESCRIPTION OF EMBODIMENTS

The present disclosure will be explained in detail through the following embodiments. The embodiments of the present disclosure are only used to describe the technical solutions of the present disclosure, and do not limit the essence and scope of the present disclosure.

Embodiments 1-4

An active ingredient (3aR,5s,6aS)-N-(3-methoxy-1,2,4-thiadiazol-5-yl)-5-(methyl(7H-pyrrolo[2,3-d]pyrimidin-4-yl)amino)hexahydrocyclopenta[c]pyrrole- 2(1H)-carboxamide was slowly added to propylene glycol, which was then mixed with caprylocaproyl macrogolglycerides, diethylene glycol monoethyl ether, and isopropyl myristate, respectively, and then polyethylene glycol 400 (PEG400), polyethylene glycol 4000 (PEG4000), glycerol, and butylated hydroxytoluene (BHT) were added. The resulting mixtures were stirred to dissolution and were rapidly cooled. The specific data is shown in Table 1.

TABLE 1

| Ingredient | Embodiment | | | |
|---|---|---|---|---|
| | 1 | 2 | 3 | 4 |
| Active Ingredient | 2 g | 2 g | 2 g | 2 g |
| Penetration Enhancer | Caprylocaproyl macrogolglycerides 2 g | Diethylene glycol monoethyl ether 2 g | Isopropyl myristate 2 g | — |
| Glycerol | 17.9 g | 17.9 g | 17.9 g | 17.9 g |
| Propylene glycol | 18.0 g | 18.0 g | 18.0 g | 20.0 g |
| PEG400 | 40.0 g | 40.0 g | 40.0 g | 40.0 g |
| PEG4000 | 20.0 g | 20.0 g | 20.0 g | 20.0 g |
| BHT | 0.1 g | 0.1 g | 0.1 g | 0.1 g |
| Ethylparaben | 0.2 g | 0.2 g | 0.2 g | 0.2 g |
| Total amount | 100 g | 100 g | 100 g | 100 g |

The ointments obtained in Embodiment 1-4 were subjected to an in vitro transdermal test to investigate the ability of the active ingredient of different formulations to penetrate the skin barrier and stay in the skin.

Preparation of excised skin: the skins of the Bama pigs in the same region were selected as the test model, hairs were shaved and the subcutaneous excess fat was peeled off. The skins were washed with PBS, and stored at −70° C. for later use.

In vitro transdermal test: the pig's skins were restored to room temperature and mounted on a Franz diffusion cell. About 0.300 g of the ointment was accurately measured, disposed in the supplying chamber, and spread evenly. A rotor and 4 mL of phosphate buffer solution (pH=7.4) were added to the receiving chamber. A multi-functional transdermal diffusion tester was used, with temperature set to 32.0° C. and a rotation speed set to 500 rpm. The sampling was carried out at 2, 4, 6, 8, 10, 12 h with a volume of 2 mL, and a phosphate buffer solution with the same volume and temperature was added at the same time. The drug contents of the samples were detected by LC-MS, and the cumulative drug transdermal amount was calculated. After completion of the test, the residual active ingredient in the supplying chamber was collected by cotton swab wiping method, the active ingredient in the stratum corneum was collected by tape peeling method, the remaining skin was shredded to collect the active ingredient, the obtained three samples containing the active ingredient were dissolved in a suitable solvent and adjusted to a constant volume, the active ingredient content was measured by HPLC method, and the recovery rate was calculated. The content of the active ingredient in the supplying chamber was referred to as residual amount, the content of the active ingredient in the stratum corneum and the skin were referred to as stratum corneum retention amount and epidermal retention amount respectively, and the cumulative transdermal amount of the active ingredient in the receiving chamber was referred to as transdermal amount. The above test was performed in 12 replicates, and the results are shown in Table 2.

TABLE 2

| Data | Embodiment | | | |
|---|---|---|---|---|
| | 1 | 2 | 3 | 4 |
| Transdermal amount (%) | 0.0067 | 0.0061 | 0.0059 | 0.0034 |
| Stratum corneum retention amount (%) | 1.54 | 2.36 | 1.76 | 1.08 |
| Epidermal retention amount (%) | 1.86 | 1.60 | 1.60 | 0.80 |
| Total skin retention amount (%) | 3.375 | 4.019 | 3.324 | 1.880 |
| Enhancing ratio | 1.80 | 2.14 | 1.77 | 1 |

Note:
the total skin retention amount = the stratum corneum retention amount + the epidermal retention amount; the enhancing ratio refers to the ratio of the total skin retention amount of the formulation with the penetration enhancer to the total skin retention amount of the formulation without the penetration enhancer.

It can be known from the above data that the active ingredient in embodiment 2 has the largest total skin retention amount and optimal enhancing ratio, which indicates that diethylene glycol monoethyl ether has better effect on enhancing the transdermal delivery of the active ingredient.

Embodiments 5-6

An active ingredient (3aR,5s,6aS)-N-(3-methoxy-1,2,4-thiadiazol-5-yl)-5-(methyl(7H-pyrrolo[2,3-d]pyrimidin-4-yl)amino)hexahydrocyclopenta[c]pyrrole- 2(1H)-carboxamide was slowly added to propylene glycol, and diethylene glycol monoethyl ether was added and mixed, then PEG400, PEG4000, glycerol and BHT were added, the resulting mixture was stirred for dissolving and rapidly cooled. The specific data are shown in Table 3.

TABLE 3

| Ingredient | Embodiment | |
|---|---|---|
| | 5 | 6 |
| Active ingredient | 2 g | 2 g |
| Diethylene glycol monoethyl ether | 2 g | 2 g |

TABLE 3-continued

| Ingredient | Embodiment | |
|---|---|---|
| | 5 | 6 |
| Glycerol | 17.9 g | 10.0 g |
| Propylene glycol | 18.0 g | 25.9 g |
| PEG400 | 30.0 g | 40.0 g |
| PEG4000 | 30.0 g | 20.0 g |
| BHT | 0.1 g | 0.1 g |
| Total amount | 100 g | 100 g |

In vitro transdermal test: the method was the same as embodiment 1, and the results are shown in Table 4.

TABLE 4

| Data | Embodiment | |
|---|---|---|
| | 5 | 6 |
| Transdermal amount (%) | 0.0018 | 0.0021 |
| Stratum corneum retention amount (%) | 2.25 | 0.90 |
| Epidermal retention amount (%) | 1.16 | 0.77 |
| Residual amount (%) | 96.59 | 98.33 |
| Recovery rate (%) | 103.23 | 97.66 |

Conclusion:

It is seen that when the ratio of PEG400 to PEG4000 is 2:1, the active ingredient has the larger epidermal retention amount, which is beneficial to the active ingredient in the pharmaceutical composition to exert its effect in skin, by comparing embodiment 5 with embodiment 2.

It is seen that when the ratio of glycerol to propylene glycol is 1:1, the active ingredient has the larger epidermal retention amount, which is beneficial to the active ingredient in the pharmaceutical composition to exert its effect in skin, by comparing embodiment 6 with embodiment 2.

Embodiment 7: Stability Study

The samples obtained in embodiment 2 were placed under an accelerated condition (30° C.±2° C./RH65%±5%) and a long-term condition (25° C.±2° C./RH60%±5%) to study their stability. The appearance, content, viscosity, and related substances were evaluated, and the viscosity was determined by the cone penetration method of general principle 0983 in Chinese Pharmacopoeia 2015 edition (Volume IV). The results are shown in Table 5.

TABLE 5 stability study results

| Evaluation conditions | Index Time (month) | Appearance | Content (%) | Cone penetration (mm) | Related substances (%) | | |
|---|---|---|---|---|---|---|---|
| | | | | | Impurity D (%) | Maximum single unknown impurity (%) | Total impurities (%) |
| 30° C. ± 2° C./ RH65% ± 5% | Original state | Off-white ointment | 98.2 | 28.3 | 0.12 | 0.04 | 0.18 |
| | 1M | Off-white ointment | 97.6 | 26.2 | 0.11 | 0.03 | 0.16 |
| | 2M | Off-white ointment | 96.8 | 27.4 | 0.12 | 0.04 | 0.17 |

TABLE 5-continued stability study results

| Evaluation conditions | Index Time (month) | Appearance | Content (%) | Cone penetration (mm) | Related substances (%) | | |
|---|---|---|---|---|---|---|---|
| | | | | | Impurity D (%) | Maximum single unknown impurity (%) | Total impurities (%) |
| | 3M | Off-white ointment | 96.8 | 27.3 | 0.13 | 0.04 | 0.19 |
| | 6M | Off-white ointment | 100.5 | 27.4 | 0.12 | 0.03 | 0.16 |
| 25° C. ± 2° C./ RH60% ± 5% | Original state | Off-white ointment | 101.5 | 35.0 | 0.12 | 0.04 | 0.19 |
| | 3M | Off-white ointment | 96.2 | 28.5 | 0.13 | 0.04 | 0.20 |
| | 6M | Off-white ointment | 98.7 | 28.2 | 0.10 | 0.04 | 0.16 |
| | 9M | Off-white ointment | 99.0 | 28.4 | 0.12 | 0.04 | 0.18 |
| | 12M | Off-white ointment | 100.3 | 28.2 | 0.10 | 0.02 | 0.15 |

The results indicate that the product obtained in embodiment 2 shows good physical stability and chemical stability under the accelerated condition (30° C.±2° C./RH65%±5%) and the long-term condition (25° C.±2° C./RH60%±5%).

What is claimed is:

1. A pharmaceutical composition comprising (3aR,5s,6aS)-N-(3-methoxy-1,2,4-thiadiazol-5-yl)-5-(methyl(7H-pyrrolo[2,3-d]pyrimidin-4-yl)amino)hexahydrocyclopenta[c]pyrrole-2(1H)-carboxamide or a pharmaceutically acceptable salt thereof, and diethylene glycol monoethyl ether wherein a content of the diethylene glycol monoethyl ether is 0.5% to 20% based on the total weight of the pharmaceutical composition.

2. The pharmaceutical composition according to claim 1, wherein the pharmaceutical composition further comprises a matrix, and the matrix is a water-soluble matrix.

3. The pharmaceutical composition according to claim 2, wherein the matrix contains polyethylene glycol 400 and polyethylene glycol 4000.

4. The pharmaceutical composition according to claim 2, wherein the pharmaceutical composition has a content of the matrix of 40% to 90%, based on a total weight of the pharmaceutical composition.

5. The pharmaceutical composition according to claim 1, wherein the pharmaceutical composition has a content of (3aR,5s,6aS)-N-(3-methoxy-1,2,4-thiadiazol-5-yl)-5-(methyl(7H-pyrrolo[2,3-d]pyrimidin-4-yl)amino)hexahydrocyclopenta[c]pyrrole-2(1H)-carboxamide or the pharmaceutically acceptable salt thereof of 0.1% to 20% based on a total weight of the pharmaceutical composition.

6. The pharmaceutical composition according to claim 1, wherein the pharmaceutical composition further comprises at least one additive selected from the group consisting of preservatives, humectants, and antioxidants.

7. The pharmaceutical composition according to claim 6, wherein the preservative is at least one selected from the group consisting of methylparaben, ethylparaben, benzoic acid, sorbic acid, phenoxyethanol, trichloro-tert-butylalcohol, phenylmercuric acetate, phenol, cresol and benzalkonium chloride.

8. The pharmaceutical composition according to claim 6, wherein the humectant is at least one selected from the group consisting of glycerol, propylene glycol, 1,3-butanediol, sorbitol, xylitol, hyaluronic acid and trehalose.

9. The pharmaceutical composition according to claim 6, wherein the antioxidant is at least one selected from the group consisting of butylated hydroxyanisole, butylated hydroxytoluene, propyl gallate and tocopherol.

10. The pharmaceutical composition according to claim 1, wherein the pharmaceutical composition comprises:
   i) 0.1% w/w to 20% w/w of (3aR,5s,6aS)-N-(3-methoxy-1,2,4-thiadiazol-5-yl)-5-(methyl(7H-pyrrolo[2,3-d]pyrimidin-4-yl)amino)hexahydrocyclopenta[c]pyrrole-2(1H)-carboxamide or the pharmaceutically acceptable salt thereof,
   ii) 0.5% w/w to 20% w/w of diethylene glycol monoethyl ether,
   iii) 40% w/w to 90% w/w of a water-soluble matrix, wherein the water-soluble matrix contains polyethylene glycol 400 and polyethylene glycol 4000, and
   iv) 20% w/w to 60% w/w of a humectant, wherein the humectant is at least one selected from the group consisting of glycerol, propylene glycol, 1,3-butanediol, sorbitol, xylitol, hyaluronic acid and trehalose.

11. A pharmaceutical composition comprising:
   i) 0.1% w/w to 20% w/w of (3aR,5s,6aS)-N-(3-methoxy-1,2,4-thiadiazol-5-yl)-5-(methyl(7H-pyrrolo[2,3-d]pyrimidin-4-yl)amino)hexahydrocyclopenta[c]pyrrole-2(1H)-carboxamide or a pharmaceutically acceptable salt thereof,
   2) 0.5% w/w to 20% w/w diethylene glycol monoethyl ether, and
   3) 40% w/w to 90% w/w of a water-soluble matrix, wherein the water-soluble matrix contains polyethylene glycol 400 and polyethylene glycol 4000.

12. The pharmaceutical composition according to claim 1, wherein the (3aR,5s,6aS)-N-(3-methoxy-1,2,4-thiadiazol-5-yl)-5-(methyl(7H-pyrrolo[2,3-d]pyrimidin-4-yl)amino)hexahydrocyclopenta[c]pyrrole-2(1H)-carboxamide has a particle size of not greater than 50 μm.

13. A method for preparing the pharmaceutical composition according to claim 1 comprising:
   i) mixing (3aR,5s,6aS)-N-(3-methoxy-1,2,4-thiadiazol-5-yl)-5-(methyl(7H-pyrrolo[2,3-d]pyrimidin-4-yl)amino)hexahydrocyclopenta[c]pyrrole-2(1H)-carboxamide or the pharmaceutically acceptable salt thereof, diethylene glycol monoethyl ether, and at least one pharmaceutical excipient selected from the group consisting of matrices, antioxidants and preservatives, to obtain a mixture, and ii) filling the mixture obtained in step i).

14. The pharmaceutical composition according to claim 2, wherein the water-soluble matrix comprises a polyethylene glycols macromolecular compound.

15. The pharmaceutical composition according to claim 3, wherein the matrix has a weight ratio of the polyethylene glycol 400 to the polyethylene glycol 4000 of 1:10 to 10:1.

16. The pharmaceutical composition according to claim 4, wherein the content of the matrix is 50% to 80% based on the total weight of the pharmaceutical composition.

17. The pharmaceutical composition according to claim 5, wherein the content of (3aR,5s,6aS)-N-(3-methoxy-1,2,4-thiadiazol-5-yl)-5-(methyl(7H-pyrrolo[2,3-d]pyrimidin-4-yl)amino)hexahydrocyclopenta[c]pyrrole-2(1H)-carboxamide or the pharmaceutically acceptable salt thereof is 1% to 10% based on the total weight of the pharmaceutical composition.

18. The pharmaceutical composition according to claim 7, wherein the pharmaceutical composition has a content of the preservative of 0.05% to 0.5% based on a total weight of the pharmaceutical composition.

19. The pharmaceutical composition according to claim 8, Wherein the pharmaceutical composition has a content of the humectant of 20% to 60% based on a total weight of the pharmaceutical composition.

20. The pharmaceutical composition according to claim 9, wherein the pharmaceutical composition has a content of the antioxidant of 0.05% to 0.5% based on a total weight of the pharmaceutical composition.

21. The pharmaceutical composition according to claim 12, wherein the particle size is not greater than 30 μm.

* * * * *